US012632485B1

(12) United States Patent
Pinter

(10) Patent No.: US 12,632,485 B1
(45) Date of Patent: May 19, 2026

(54) SYSTEMS AND METHODS FOR INTERACTIVE DIGITAL EXERCISES WITH CREATIVE ARTS

(71) Applicant: MindClay, Santa Barbara, CA (US)

(72) Inventor: Marco Pinter, Santa Barbara, CA (US)

(73) Assignee: MindClay, Santa Barbara, CA (US)

( * ) Notice: Subject to any disclaimer, the term of this patent is extended or adjusted under 35 U.S.C. 154(b) by 0 days.

(21) Appl. No.: 18/932,364

(22) Filed: Oct. 30, 2024

Related U.S. Application Data

(60) Provisional application No. 63/546,316, filed on Oct. 30, 2023.

(51) Int. Cl.
  G06F 16/338         (2019.01)
  G06F 16/334         (2025.01)
  G16H 20/70          (2018.01)
(52) U.S. Cl.
  CPC ........ G06F 16/338 (2019.01); G06F 16/3344 (2019.01); G16H 20/70 (2018.01)
(58) Field of Classification Search
  CPC .... G06F 16/338; G06F 16/3344; G16H 20/70
  See application file for complete search history.

(56) References Cited

U.S. PATENT DOCUMENTS

| | | | | |
|---|---|---|---|---|
| 2012/0063654 A1* | 3/2012 | Kim | ....................... | G06Q 50/20 |
| | | | | 382/128 |
| 2022/0068462 A1* | 3/2022 | Dolan | ..................... | G10L 25/63 |

FOREIGN PATENT DOCUMENTS

WO      WO-2021214554 A1 *   10/2021   ............. G16H 50/70

\* cited by examiner

*Primary Examiner* — Aleksandr Kerzhner
*Assistant Examiner* — Aryan D Toughiry
(74) *Attorney, Agent, or Firm* — Knobbe, Martens, Olson & Bear, LLP

(57) ABSTRACT

A computer-readable medium stores instructions that cause one or more processors to perform mental wellness activities. The activities can include providing a user interface to receive inputs about a user's challenges and strengths, generating a query to a large language model (LLM) to create a narrative where challenges are addressed based on strengths, and displaying the narrative. The activities can include providing an interface for a therapeutic exercise, showing the exercise's intention, guiding the user through the exercise, and collecting feedback afterward. The activities can include recommending therapeutic activities by analyzing user data to identify preferences or emotional states. Based on the amount of aggregate user data, either predefined rules or collaborative filtering is used to make personalized activity recommendations.

18 Claims, 8 Drawing Sheets

210

230

SYSTEMS AND METHODS FOR INTERACTIVE DIGITAL EXERCISES WITH CREATIVE ARTS

CROSS-REFERENCE TO RELATED APPLICATIONS

The present application claims priority to U.S. Provisional Application No. 63/546,316, filed on Oct. 30, 2023, which is incorporated by reference in its entirety.

TECHNICAL FIELD

Disclosed embodiments pertain to the field of digital mental health interventions, focusing on the integration of creative arts therapies with advanced artificial intelligence (AI) or machine learning (NIL) technologies to enhance user engagement and mental wellness. Some implementations employ AI-driven methodologies, including story framing, interactive poetry, and intelligent recommender systems, to deliver personalized therapeutic experiences. Some implementations are designed to use multimodal data from activities spanning multiple media modalities. This approach addresses the low engagement and high attrition rates prevalent in traditional mental health applications by providing a customizable, engaging, and therapeutically valuable user experience. Some implementations are particularly adept at utilizing creative arts including music, visual arts, movement, and writing, to facilitate a personalized mental wellness journey through an intuitive digital platform.

BACKGROUND

The mental health crisis continues to escalate globally, exacerbated by the isolation and stress of modern life. Traditional mental health interventions often struggle with low engagement and high attrition rates, failing to maintain user interest and participation. This is particularly true in the context of digital mental health platforms, where impersonal interfaces and lack of customization lead to disengagement. Additionally, the one-size-fits-all approach of many existing applications does not address the diverse needs of various user demographics, which include cultural, psychological, and situational differences.

Creative arts therapies have been recognized for their effectiveness in improving mental health, leveraging activities in music, art, dance, and writing to engage users in therapeutic processes that are both enjoyable and healing. However, the translation of these therapies into digital formats has often not capitalized on their potential, offering static and non-interactive content that fails to engage users deeply.

Furthermore, the importance of personalization in therapeutic applications is increasingly acknowledged. Personalized interventions are known to be more effective as they can adapt to the unique circumstances and preferences of each user, thus increasing engagement and the likelihood of positive outcomes. Yet, many mental wellness apps lack the sophisticated technology needed to implement true personalization, relying instead on rudimentary categorizations and linear content delivery.

The advent of artificial intelligence (AI) in healthcare presents new opportunities for innovation in mental health technologies. AI can process vast amounts of data from user interactions to learn individual preferences and needs, enabling the delivery of highly personalized content.

Despite this potential, the integration of AI with creative arts therapies in a digital platform remains underexplored.

In light of these challenges and opportunities, there is a clear need for a mental wellness platform that combines the engaging power of creative arts therapies with the personalization capabilities of AI.

SUMMARY

In some implementations, a comprehensive digital platform or system (sometimes referred to as MindClay) designed to enhance mental wellness through the integration of creative arts therapies is disclosed. The platform can encompass a variety of modalities, including music, visual art, dance-movement, and writing, utilizing an intelligent framework to dynamically adapt these therapies to individual user needs. The platform can employ advanced artificial intelligence (AI) or machine learning (ML) technologies to analyze and understand user interactions and preferences, facilitating a highly personalized therapeutic journey.

The platform can include an innovative recommender system. Rich data and multimodal data can be utilized to tailor therapeutic activities specifically to each user, considering factors such as past interactions, current emotional states, and long-term therapeutic goals. Designed to continuously evolve, the platform can refine its recommendations through ongoing learning from accumulated user data, ensuring that the therapeutic content remains optimally aligned with the user's evolving mental health needs. The platform can dynamically adapt to user feedback and interaction patterns, employ an intelligent recommender system to suggest personalized therapeutic activities, and utilize rich data and multimodal data to enhance user engagement and treatment efficacy.

In some implementations, disclosed is a non-transitory computer readable medium storing instructions that, when executed by one or more processors, cause the one or more processors to: provide a user interface with at least one first input configured to receive first data indicating a set of challenges being faced by a user and at least one second input configured to receive second data indicating a set of strengths of the user; receive, via the user interface, the first data and the second data; generate a first query to an application program interface (API) of a large language model (LLM), the first query requesting that the LLM generate a textual narrative about the user in which the set of challenges indicated by the first data is overcome based on the set of strengths indicated by the second data; provide the first query to the API of the LLM and cause the LLM to generate the textual narrative; receive the textual narrative from the API in response to providing the first query; and output the textual narrative to the user interface.

In some implementations, the one or more processors are further caused to: receive, via the user interface, third data indicating identity of the user; and generate the first query further based on the third data to cause the LLM to generate the textual narrative that further includes the third data.

In some implementations, the first query includes: a first prompt requesting the LLM to generate the textual narrative about the user identified by the third data; a second prompt indicating that challenges faced by the user include the first data; and a third prompt indicating that strengths of the user include the second data.

In some implementations, the first query further includes a fourth prompt specifying a time frame limitation for the textual narrative and a length limitation of the textual narrative.

In some implementations, the at least one first input includes at least one first text box, and wherein the at least one second input includes at least one second text box.

In some implementations, the one or more processors are further caused to: provide another user interface with at least one third input configured to receive a first poetry line from the user indicative of a problem that the user faces; receive, via the another user interface, the first poetry line from the user; generate a second query to the API of the LLM, the second query requesting that the LLM generate a second poetry line responsive to the first poetry line; provide the second query to the API of the LLM and cause the LLM to generate the second poetry line; receive the second poetry line from the API in response to providing the second query; and output the second poetry line to the another user interface by appending the second poetry line to the first poetry line.

In some implementations, the one or more processors are further caused to: receive, via the user interface, a third poetry line from the user, the third poetry line being created by the user to maintain a theme and narrative progression of a poem that includes the first and second poetry lines; generate a third query to the API of the LLM, the third query requesting that the LLM generate a third poetry line responsive to the first, second, and third poetry lines; provide the third query to the API of the LLM and cause the LLM to generate a fourth poetry line that maintains the theme of the poem; receive the fourth poetry line from the API in response to providing the third query; and output the fourth poetry line to the another user interface by appending the fourth poetry line to the first, second, and third poetry lines.

In some implementations, the one or more processors are further caused to output to the user interface information indicating an intention of generating and outputting the textual narrative prior to receiving the first data and the second data.

In some implementations, disclosed is a non-transitory computer readable medium storing instructions that, when executed by one or more processors, cause the one or more processors to: provide a user interface for an exercise directed to a therapeutic activity for improving mental wellness of a user; output to the user interface information indicating an intention of the exercise, the intention indicating a therapeutic concept of the exercise directed to improving mental wellness of the user; subsequent to outputting information indicating the intention of the exercise, output to the user interface the exercise, the exercise involving user interacting with the user interface; and subsequent to completion of the exercise by the user, prompt the user via the user interface to provide reflective input describing psychological or emotional significance of the exercise experience to the user.

In some implementations, the therapeutic activity includes one or more of drawing, writing, dance, or music.

In some implementations, the one or more processors are further caused to: provide on the user interface an input configured to permit the user to draw a challenge; and in response to the user providing a drawing of the challenge via the input, modify the drawing so that the challenge fades away.

In some implementations, the challenge fades away while the user is drawing the challenge.

In some implementations, the user interface includes one or more controls configured to adjust one or more parameters of the challenge fading away.

In some implementations, the one or more parameters include a speed of the challenge fading away.

In some implementations, the one or more controls include a slider.

In some implementations, disclosed is a non-transitory computer readable medium storing instructions that, when executed by one or more processors, cause the one or more processors to: collecting user data related to one or more therapeutic activities for improving mental wellness of a user, the user data including one or more of textual data for natural language processing, visual data from user-drawn features, audio data from user-created music, or motion data from user movements; extract a plurality of features from the user data, the plurality of features reflecting one or more of preferences or emotional states of the user, wherein extracting the plurality of features includes one or more of: applying natural language processing to textual data, applying visual analysis to user-drawn features, applying audio analysis to user-created music, or applying motion analysis to captured motion data; based on the plurality of features, generate a recommendation for a therapeutic activity for improving mental wellness of a user by: in response to a determination that an aggregate data collection threshold across a plurality of users has not been satisfied, apply one or more predefined rules to the plurality of features to generate the recommendation for the therapeutic activity; and in response to a determination that the aggregate data collection threshold across the plurality of users has been satisfied, apply similarity-based analysis to the plurality of features to generate the recommendation for the therapeutic activity; and output the therapeutic activity to a user interface and cause the user to perform the therapeutic activity.

In some implementations, the one or more processors are further caused to: subsequent to completion of the therapeutic activity, receive, via the user interface, feedback data relating to the therapeutic activity from the user; and based on the feedback data, adjust a recommendation for a subsequent therapeutic activity to be performed by the user.

In some implementations, the feedback data includes an adjustment of a parameter of the therapeutic activity, and wherein the subsequent therapeutic activity includes the parameter modified by the adjustment.

In some implementations, similarity-based analysis includes: grouping the user with at least one another user that shares at least one characteristic with the user; and generating the recommendation for the therapeutic activity based on another therapeutic activity previously recommended to the another user.

In some implementations, the therapeutic activity includes one or more of drawing, writing, dance, or music.

Methods implementing the instructions of any of the preceding paragraphs are disclosed.

BRIEF DESCRIPTION OF THE DRAWINGS

In the following description, various implementations will be described. For purposes of explanation, specific configurations and details are set forth in order to provide a thorough understanding of the implementations. However, it will also be apparent to one skilled in the art that the implementations may be practiced without the specific details. Furthermore, well-known features may be omitted or simplified in order not to obscure the implementation being described.

DETAILED DESCRIPTION

Overview

Figure 1:
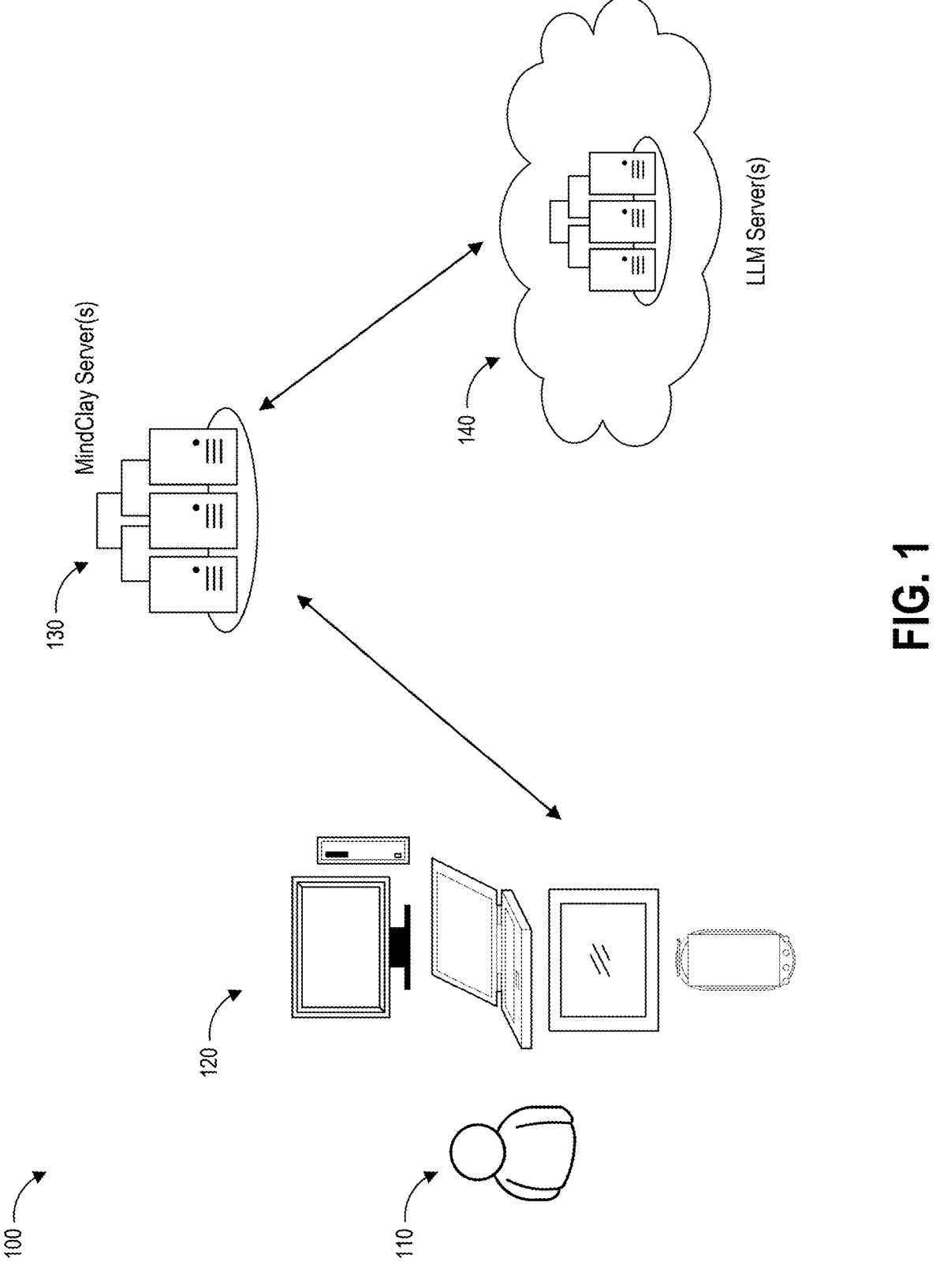
FIG. 1 illustrates a block diagram of a system for enhancing mental wellness.

FIG. 1 illustrates a block diagram of a system 100 for enhancing mental wellness (sometimes referred to as Mind-Clay). The system 100 can include a computing device 120 operated by a user 110. The computing device 120 can be one or more of a personal computer, laptop, tablet, smartphone, a wearable device, or the like. The computing device 120 can include one or more memories and one or more processors that store and execute instructions for enhancing mental wellness. As described herein, the user 110 can interact with such instructions, for instance, via one or more user interfaces. For example, a user interface can be part of an application (or app), web application, or the like. One or more user interfaces can provide one or more of visual, auditory, or tactile input or outputs.

The system 100 can include a plurality of users 110 operating a plurality of respective computing devices 120.

Any computing device 120 can communicate data to and receive data from one or more computing devices 130, which can be one or more servers. Data can include data provided by the user 110 via the user interface. The computing device 120 can communicate with the one or more servers 130 via one or more networks. The one or more servers 130 can include a database of user's artistic creations and a secure database of rich user data for generating recommendations. The one or more servers 130 can store and execute instructions to access data from all users 110, aggregate the data, and generate recommendations. The one or more servers 130 can include one or more memories and one or more processors.

One or more computing devices 140 can communicate with the one or more servers 130 via one or more networks. The one or more computing devices 140 can be cloud computing devices (such as, one or more servers). The one or more computing devices 140 can implement one or more large language models (LLMs) for performing natural language tasks. The LLM(s) can assist with enhancing mental wellness, as described herein. The one or more computing devices 140 can include one or more memories and one or more processors.

One or more computing devices 130 can interface with the one or more computing devices 140 via an application program interface (API) provided by the LLM(s). As described herein, the API can receive a query and provide a response. In some implementations, the LLM(s) can be OpenAI's GPT.

The system 100 can deliver a personalized mental wellness experience via providing provide one or more of the following features to ensure that users 110 can engage with therapeutic activities anytime and anywhere, which can be critical for those needing flexible support for their mental health.

AI Story Framing and Outcome: Utilizes narrative techniques guided by AI to frame user experiences and outcomes in a therapeutic context. This can have a profound impact, as a user who is depressed and feels hopeless can see that there can be positive outcomes over time to all the challenges the user is experiencing.

AI Poetry Generation: Employs AI to assist users in creating poetry as a form of therapy, fostering emotional expression and processing.

Intention and Integration: Features that allow users to set goals and reflect on their experiences to integrate the therapeutic benefits of activities. This can be unique in its treatment of creative digital activities (such as, drawing, writing, and making music) to frame the activities with intention and integration, which can provide a much greater wellness impact.

Global Community Activities: A community-driven area that allows users to contribute to collective artwork, enhancing the sense of connection and community.

Impermanence Activity: An activity that helps users visualize and gradually let go of stressors, using visual fading techniques to symbolize the impermanence of emotional states.

Recommender System: Harnesses user data to provide targeted recommendations, improving the personal relevance of the therapeutic activities offered.

Data Collection

One of distinct advantages of the system 100 over existing meditation-based wellness apps is due to the rich data the system collects from, among others, interactive writing, art-making, music-making, and body movement activities. Data collection can go well beyond the limited data tracked by existing meditation-based apps, which generally capture basic interactions (such as, audio selections and listening time). Examples of data collected by the system 100 include one or more of the following:

1. Demographic Data & Mental Health Questionnaires: provides a basic understanding of the user's background and initial mental state (including needs around anxiety, relationship issues, or the like).

2. Specific Activity Choices & Times of Day: allows tracking of which specific activities a user likes, and insights into their daily routines and preferred times.

3. Higher level groupings:

3a. Format choices, such as shorter vs. longer content or content organized as individual versus content in series.

3b. Modality: art vs. music vs. movement vs. writing.

4. Advanced Data Modalities:

Writing: beyond just content, the sentiment and theme analysis can offer windows into the user's thoughts, emotions, and well-being.

Music: understanding tempo, instrument choices, or musical mood can reflect emotional states and preferences Movement: posture and movement patterns can be incredibly telling, reflecting everything from energy levels to emotional states like sad, agitated or calm.

Art: color choices, stroke styles, and patterns can be indicative of mood, mindset, and even specific emotional triggers.

In some cases, particularly data items 3b and 4 collected by the system 100 can allow for developing much deeper insights into the user's mental health. The system 100 can take advantage of combinations and correlations, since many activities combine multiple modalities in the same activity, for example, art and writing or movement and sound analysis. Those activities can provide such combinations of rich data, thereby providing, in aggregate, multimodal data.

Recognizing the importance of explainability, privacy, and accountability in building trust for wellness systems, especially within the mental health realm, the system 100 can prioritize these metrics. In terms of privacy, users can have the option to opt in for data collection. For greater transparency in explainability, when a user receives a suggestion, such as a drumming activity, the system 100 can provide a rationale (such as, indicating its link to a previously completed activity). All user data can be encrypted and stored by the one or more computing devices 130.

Activities

A broad range of activities can be offered by the system 100, including without limitation, one or more of visual art, music, movement, and creative writing. Examples of activities are illustrated in FIGS. 2A to 2D.

Figure 2A:
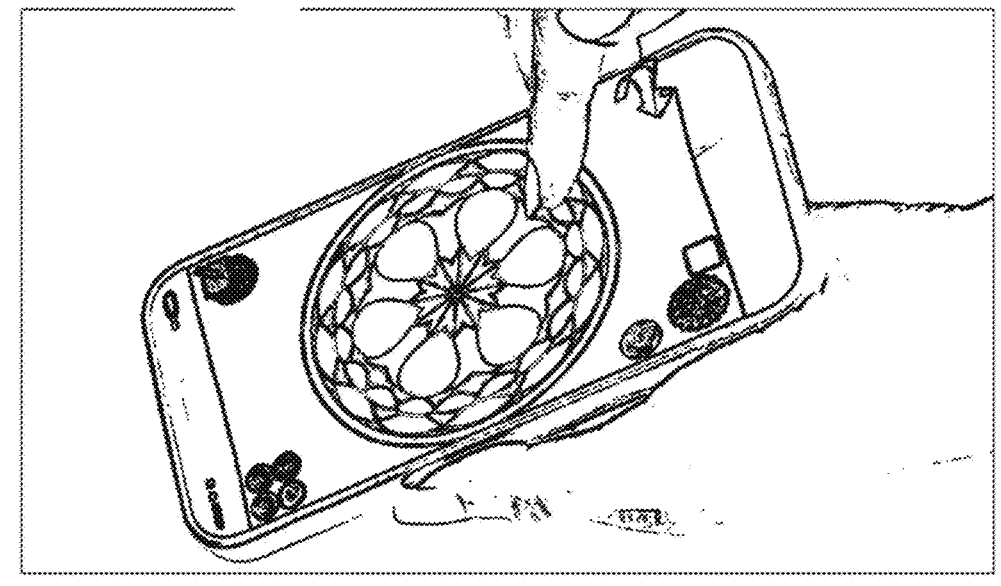
FIGS. 2A to 2D depict various activities offered by the system illustrated in FIG. 1.

With reference to FIG. 2A, mandala maker activity 210 can be provided to a user 110. Studies have shown that creating mandalas is effective in addressing anxiety and depression. Mandala maker activity 210 can collect multimodal data for one or more of color choice, finger movement speed or jitter, or integration text.

Figure 2B:
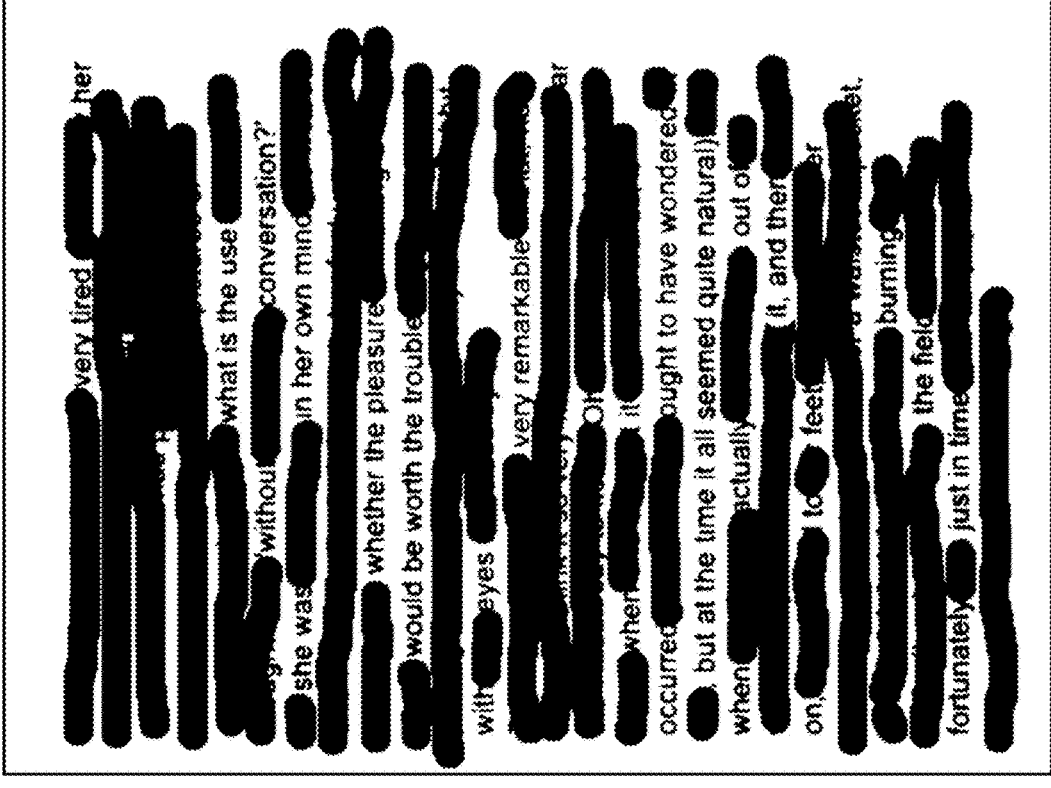

With reference to FIG. 2B, blackout poetry activity 220 can be provided. Poetry writing has many proven mental wellness benefits. Blackout poetry can lower the barrier for entry by choosing words from existing literary passages. Blackout poetry can collect multimodal data for one or more of finger movement speed or jitter or choice and pattern of revealed words.

Figure 2C:
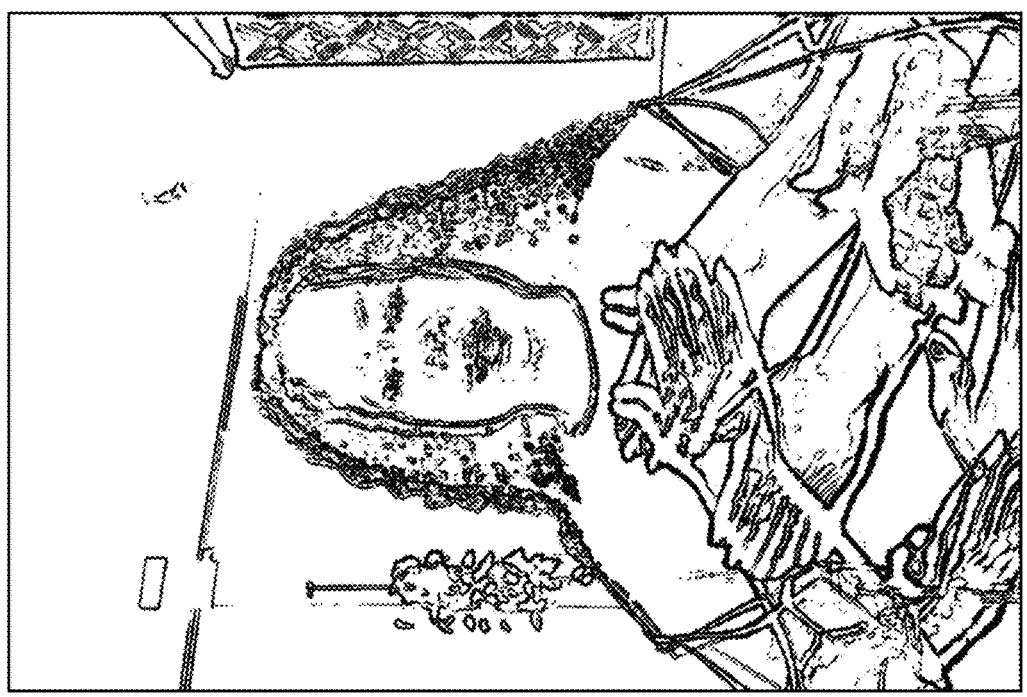
Figure 2C:

With reference to FIG. 2C, time dilation activity 230 can be provided. In the illustrated example, time dilation allows three versions of body outline, over time, to be overlaid. The guided activity can evoke a feeling of community support. Time dilation can collect multimodal data for one or more of limb movement or integration text.

Figure 2D:
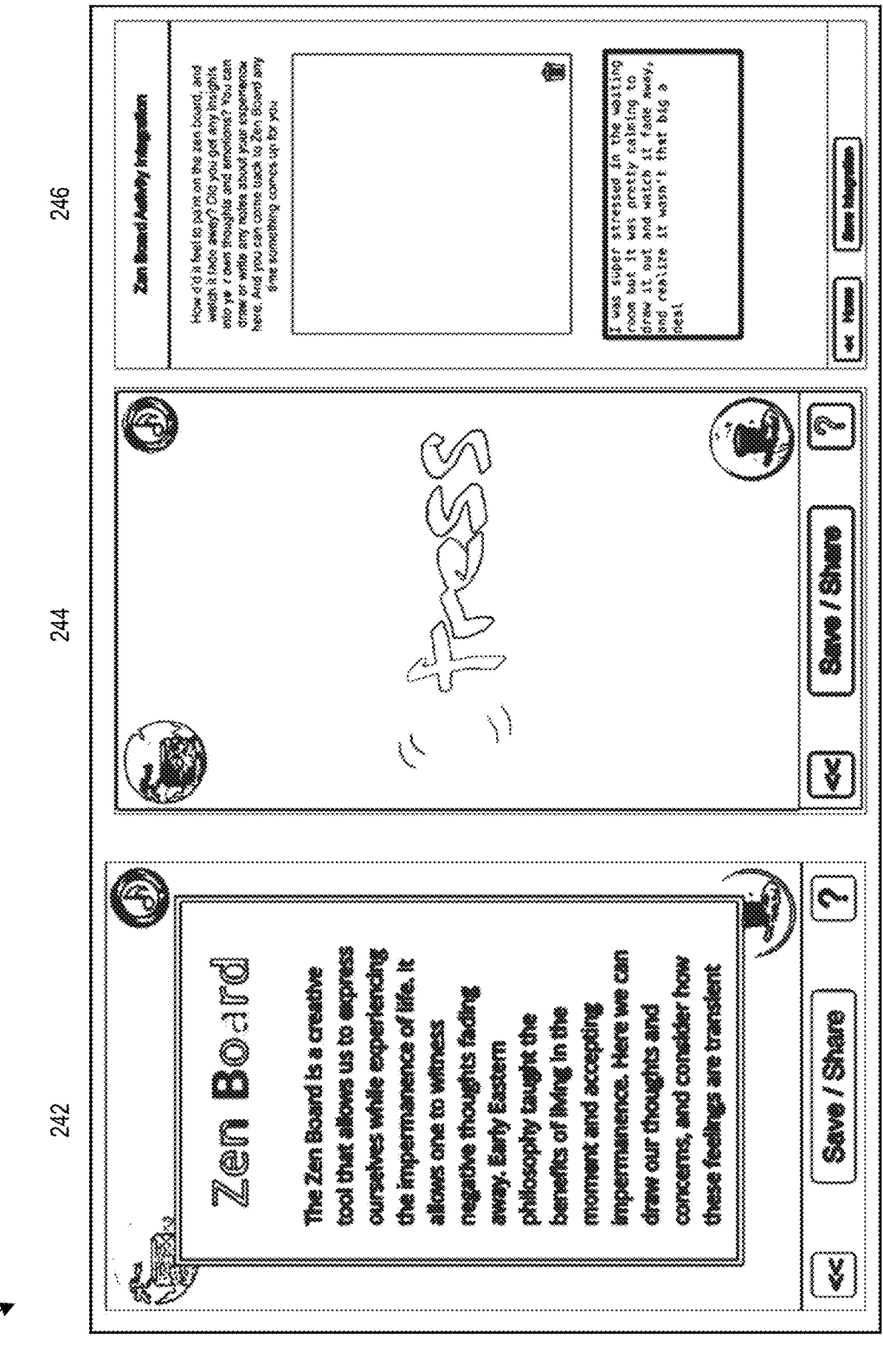

With reference to FIG. 2D, Zen Board activity 240 can be provided. Zen Board can utilize the therapeutic concept of "decentering" to encourage users 110 to consider the transient nature of emotions. Once a user 100 has read the introduction (illustrated as 242), the user can put the therapeutic concept into practice by drawing a challenge the user has been feeling (illustrated as "Stress") and watching the challenge fade away (illustrated as 244). The challenge can fade away while a user 110 is drawing the challenge (or, in some cases, after the user 110 has completed the drawing). Parameters of fading, such as, speed or size, can be adjusted by the user 110 via one or more user interface controls (such as, one or more sliders). Upon completion, the user 110 is prompted to journal that experience (illustrated as 246), wherein they are prompted to reflect on the psychological or emotional impact of their experience with the activity. This activity sequence is in contrast to existing non-therapeutic creative apps, which have no intention setting or integration, which can be critical in the creative arts therapy process.

The system 100 has an advantage over existing meditation-oriented apps in that the system 100 can be utilized by a user 110 at any time to practice therapeutic concepts, such as, mindfulness or optimism in busy settings (including in stressful situations, such as, waiting in line at the DMV or airport). This is in contrast to existing meditation-based apps, which require a quiet, solitary setting.

Each activity can include 1) an introduction which highlights a therapeutic concept and sets intention for the exercise; 2) the therapeutic activity itself; and 3) an integration page offering a journaling or drawing prompt that can provide meaningful connections to lived experience (such as, psychological or emotional significance of the exercise experience to a user).

AI Story Framing and Outcome

AI story framing and outcome component of the system 100 involves generating personalized narratives using the LLM(s). AI story framing and outcome can process a user's 100 inputs regarding personal challenges and interface with the LLM(s), which can generate narratives for overcoming these challenges. The narratives can be provided to the user 110. As described herein, interfacing with the LLM(s) can be performed via an API.

The system 100 can be configured to prompt the user 100 to enter specific challenges the user faces into, for instance, three distinct (or less or more) input fields of a user interface provided on the computing device 120. These inputs can be collected and processed by the system (for example, by the one or more computing devices 130) and formatted into a structured API request. This request can incorporate the challenges into a narrative framework, using predefined templates combined with user-specific data.

An example AI story framing and outcome can involve the following tasks:

1. Input Collection: The user 110 is prompted to enter three (or more or less) challenges the user is currently facing in the user's life. The user 110 is also prompted to enter three (or more or less) strengths. The user 110 enters challenges and strengths into text boxes, which are tagged for processing. The user 110 also provides identifying information (such as, name, pronouns, or the like).

2. Query Construction: The one or more computing devices 130 concatenates these inputs into a string that forms part of an API query. For example, the API query can be as follows:

$storyPrompt="Write a story focused only on the following details about $firstName, who uses $pronouns.";

$storyPrompt.=$challenges?"They have these challenges: $challenges.": " ";

$storyPrompt.=$strengths?"Their strengths are $strengths.": " ";

$storyPrompt.="The story should closely adhere to these specifics without inventing additional details about $firstName's personal history, job, or other aspects of life not mentioned. The story should illustrate how they overcome their challenges, keeping within a year or two, and should be around 400 words.";

3. Narrative Generation: The query is sent to LLM(s) via an API (such as, OpenAI's GPT). The LLM(s) processes the query and returns an optimistic narrative showcasing a scenario where the challenges are overcome. The LLM(s) can be configured to process natural language inputs and generate narrative outputs.

4. Output Presentation: The generated narrative is received and presented to the user through the user interface.

Figure 3:
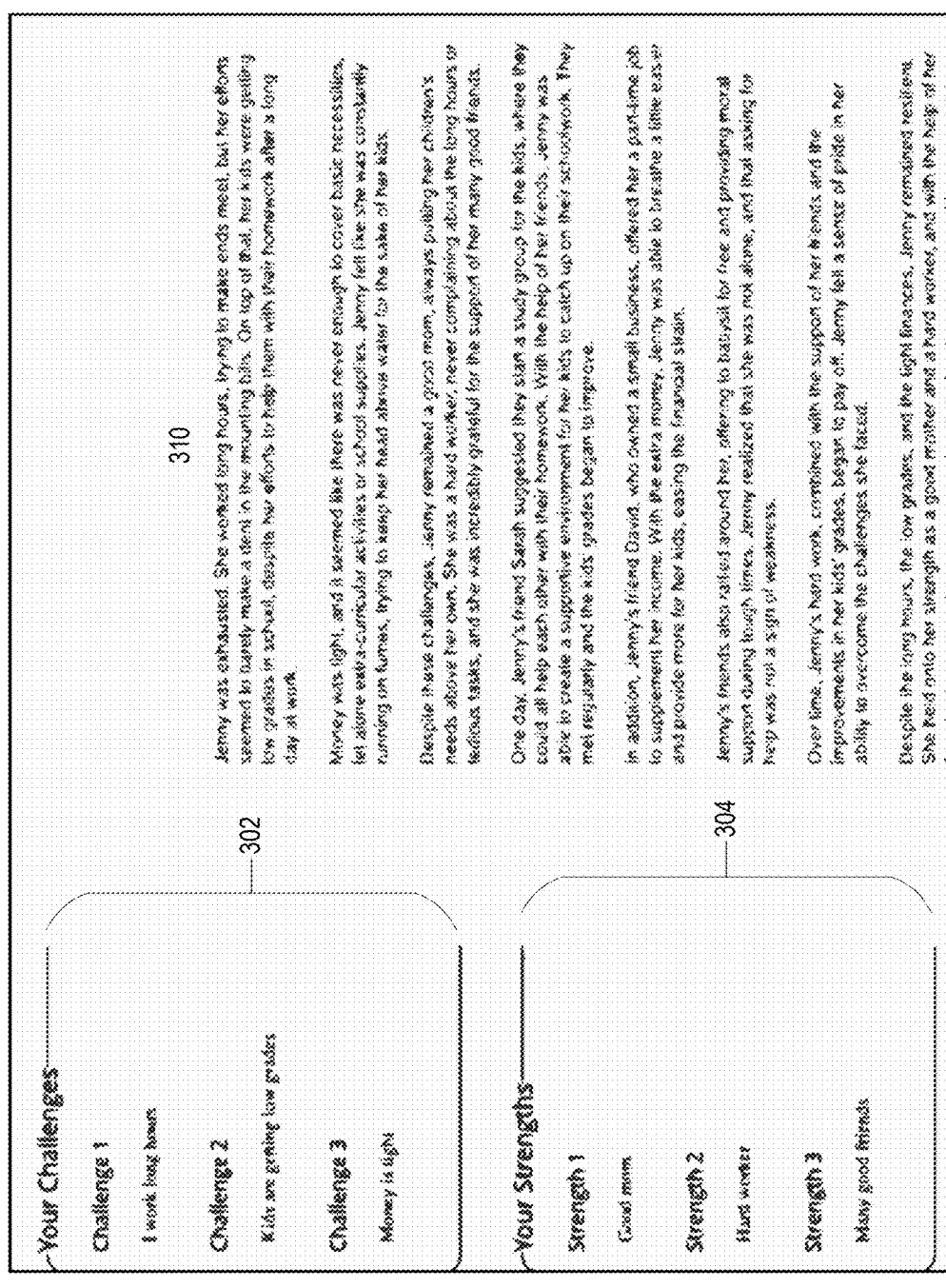
FIG. 3 depicts AI story framing and outcome offered by the system illustrated in FIG. 1.

FIG. 3 illustrates an example user interface 300 of AI framing and outcomes for a user named Jenny. The user interface 300 includes input collection fields 302 and 304 (such as, text boxes) for receiving information regarding Jenny's challenges and strengths. The challenges include: "I work long hours," "Kids are getting low grades," and "Money is tight." The strengths include: "Good mom," "Hard worker," and Many good friends." Output field 310 provides an excerpt of a narrative generated by the LLM(s).

AI framing and outcomes implemented by the system 100 can involve secure data transmission (for instance, between the computing device 120 and the one or more computing devices 130) to ensure that user inputs are safely handled and responses are accurately parsed. The user interface can be designed to be intuitive, with clear labeling and responsive input fields tailored for ease of use and accessibility. The API of LLM(s) can be configurable and the LLM(s) can be capable of processing natural language inputs and generating narrative outputs.

AI Poetry Generation

The system 100 can facilitate collaborative poetry creation between a user 110 and the system (such as, with the assistance of the LLM(s)). The user 100 can be allowed to articulate personal challenges through poetry, with the system 100 generating alternating lines based on user inputs, creating a structured poetic dialogue. AI poetry generation can engage users in expressing and processing personal issues through the medium of poetry, utilizing the LLM(s) to assist in the creative process. AI poetry generation can leverage the language processing capabilities of the LLM(s) to interpret user-submitted issues and generate contextually relevant poetry lines.

Figure 4:
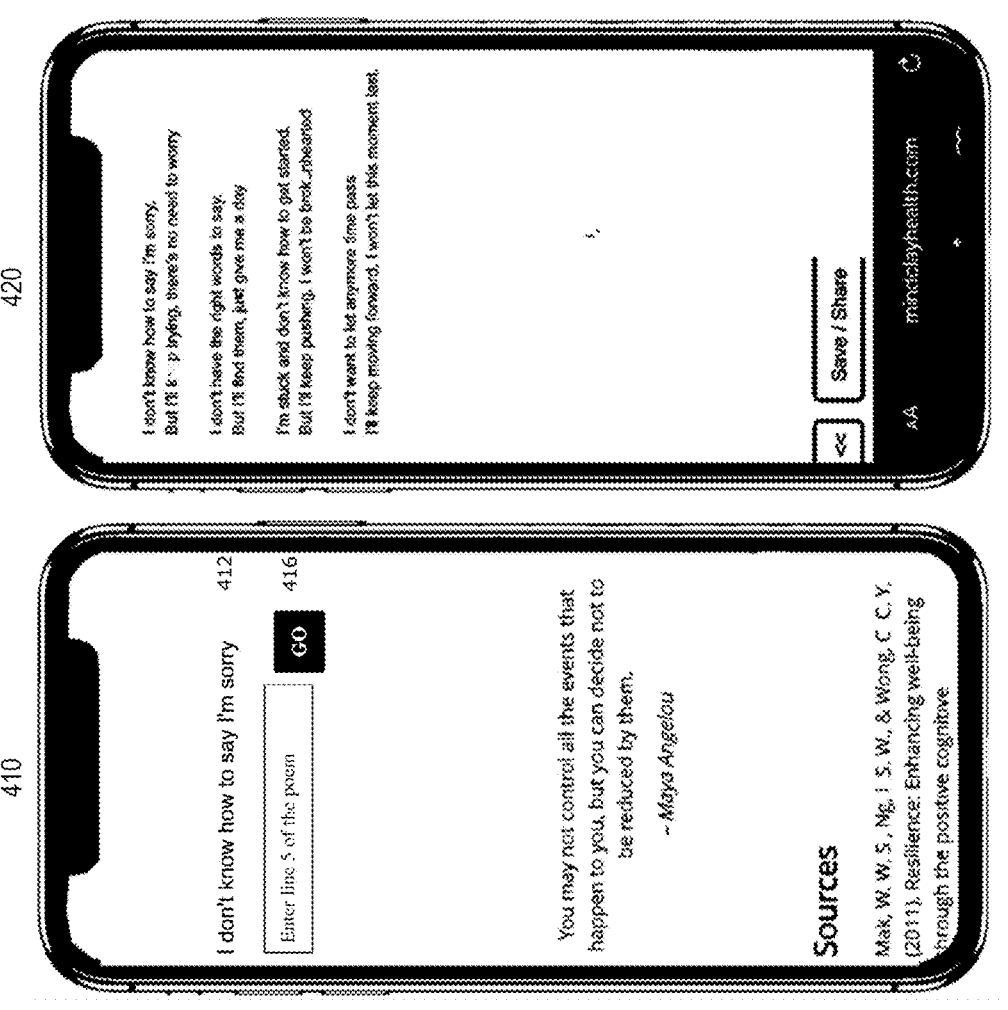
FIG. 4 depicts AI poetry offered by the system illustrated in FIG. 1.

With reference to FIG. 4, an example AI poetry generation 400 can involve the following tasks:

1. User Input Collection: A user 110 begins by describing a personal issue the user is facing via a text input field in a user interface (410) of the device 120. This input is captured and formatted into a structured string (or prompt) that is sent to the LLM(s) API (for instance, by the one or more computing devices 130). Interaction with the API can be as follows: "John is experiencing the following problem. [insert problem string]. Write the first line of a therapeutic poem about self-encouragement, that is no more than 20 syllables, and addresses that challenge. Do not make up new material." The prompt to avoid making up new material is important, as LLM(s) have a tendency to do that, which distracts from the user experience.

2. Initial Line Generation: Based on the user's description the surrounding prompt, the LLM(s) generates the first line of the poem (412), which reflects themes or sentiments related to the described issue. This line is sent back to the computing device 120 and provided to the user 110 on the user interface.

3. User and LLM Interaction: The user 110 then contributes the next line of the poem, continuing from the narrative or theme introduced by the LLM(s) (416). This user-generated line is sent back to the one or more computing devices 130, where it is appended to the initial line and resent to the LLM(s). Interaction with the API can be as follows: "John is experiencing the following problem. [Insert problem string]. The following lines of a poem about that issue are presented here. Write the next line. [Insert existing lines]. The following lines of a therapeutic poem about self-encouragement, that addresses that issue, are presented here. Follow the theme of the prior lines and do not make up new material. Write the next line. [Insert existing lines]." The LLM(s) processes the prompt to generate the subsequent line, ensuring thematic consistency and narrative progression.

4. Iterative Collaboration: This process is repeated, with the user 110 and the LLM(s) alternating lines, until the poem reaches a predefined length (such as, 12 lines or less or more), thus completing the poem (as shown in 420).

The system 100 can integrate with the LLM(s) via an API, capable of understanding and generating natural language constructs based on dynamic user inputs. Server-side scripting executed on the one or more computing devices 130 can handle the concatenation of user inputs and LLM(s) outputs, managing the sequence of interactions and ensuring data integrity across the communication layers. The user interface can provide a responsive text input area and display the poem as it is being constructed, including interactive prompts that guide the user 110 through the poetry creation process.

In some implementations, a user can start by writing the first line of the poem directly (such as, the line 412), without explicitly describing the user's issue. A prompt can be provided to the LLM(s): "Write the next line of this poem, which is about self-encouragement, and is therapeutic. The line should rhyme the one just prior, or be close. Follow the theme of the prior line(s) and don't make up new material. Here is poem so far: [Insert string]." The LLM(s) can then infer the underlying theme or problem from the poetic content provided and generate the next line accordingly. This reverse process emphasizes the LLM(s)'s capability to derive contextual understanding from poetic expressions, enhancing the creative collaboration.

Recommender System

The domain of interactive activity-based mental wellness, particularly one that encompasses diverse modalities like poetry-writing, live movement, drawing, and music-making, is uncharted in digital platforms. Creating a system that integrates bootstrapping, rich data analytics, and collaborative filtering (which is a type of similarity-based analysis) in a mental wellness app is a pioneering endeavor. One of the challenges, for example, is considerable uncertainty around processing the complex and potentially ambiguous data that will be collected. Integrating techniques like natural language processing (NLP), visual, sound, and movement analysis for real-time user profiling in a mental wellness context is quite challenging.

Human emotions, moods, and their expressions through activities like writing, drawing, or music-making are deeply complex. It is possible that, despite the richness of the data, consistent and generalizable patterns may not emerge that can predict engagement. Vast individual differences can make it challenging to find overarching patterns that apply broadly. Further, emotional states can be transient. A pattern observed one week might not hold the next, making it hard to differentiate between long-term behaviors and short-lived emotional responses.

However, if the technical goals are not reached, the personalized engagement profiles will not be achieved and user engagement will be significantly hampered.

The system 100 can solve these and other challenges by providing activity recommendations specifically designed based on analysis of extensive rich data and multimodal data from user interactions to suggest personalized therapeutic activities that enhance mental wellness. The system 100 can utilize the rich data set described herein to provide recommendations. This data includes, but is not limited to, textual data for natural language processing (NLP), visual data from user-created drawings, audio data from user-generated music, and motion data captured during physical interactions. The system 100 can use these varied data sources-NLP for text, image analysis for drawings, audio analysis for music features, and motion capture analysis for physical movement-allowing for a nuanced understanding of user engagement and emotional expression across different modalities. The multimodal data (sometimes referred to as combinatorial data) can be used for more detailed personalization and precision in content recommendations.

During initial deployment when there is limited data in the system 100, the system 100 employs bootstrapping through expert-driven rules. The system 100 can be bootstrapped with expert rules created in consultation with subject matter experts in the field of creative arts therapy.

This can serve to address the "cold start" problem for new users, where there is limited data available. Expert rules may include one or more of the following:

For a member that is stressed—determined by mental health questionnaire and/or sentiment analysis on writing samples—the system 100 can recommend music activities with gentle, harmonious instruments.

If a user's writings frequently express feelings of loneliness or isolation, the system 100 can recommend collaborative or group activities within the app, like shared art projects or group song creations.

A user who often selects soft, melodic instruments like flutes might be guided towards gentle art drawing activities, reflecting a possible preference for calmness.

If a user consistently creates slow, melancholic rhythms, the system 100 can first recommend activities that resonate with this mood. Gradually, the system 100 can suggest more uplifting and rhythmic movement activities to elevate the user's mood, employing the iso principle from music therapy, which validates the user's mood and then gently shifts it in the desired direction.

In order to achieve better person-activity fit, users with a high score in the "Openness to Experience" trait from the Big 5 personality test often correlate with creativity and a broader range of interests. Such users can be presented with a more heterogenous, diverse array of activity options. In contrast, users scoring lower on this trait likely prefer a more homogenous, narrowed set of activities aligned with their specific values and interests, and the system 100 can tailor its recommendations accordingly.

Responsive to the available data reaching a data collection threshold across a number of users, the system 100 can transition to utilizing collaborative filtering techniques. This approach can leverage the strengths of these technologies, combining different users' tastes to create strong personalized recommendations that optimize user engagement. While expert rules may offer a foundational understanding, they can be narrow and often favor people in the middle of the bell curve (such as, popular). In contrast, collaborative filtering can bring out intricate and sometimes non-intuitive (or even counter-intuitive) patterns in a user behavior, offering insights that can further refine and personalize the experience for users and allow for academic research on cognitive and personality styles and their relation to creative activities. These patterns can emerge once there is a threshold number of users. Collaborative filtering can group users with similar behaviors and utilize the groups to make recommendations. For example, user 1 and user 2 can be determined to have similar behaviors and activity 1 previously recommended to user 1 can be subsequently recommended to user 2. Examples of the types of patterns that could emerge automatically from the collaborative filtering process include one or more of the following:

Users who write about nature may often opt for instruments that produce nature-like sounds (e.g., rainmaker, wind chimes). This would result in suggesting nature-themed activities across modalities.

Users who create abstract art may also prefer irregular, non-traditional music rhythms. Suggested activities would then include avant-garde music sessions to those who engage deeply with abstract art.

Users who draw using vibrant colors in the morning may tend to opt for energetic music sessions in the evening.

Users who frequently draw geometric patterns may have a penchant for writing structured poems, like sonnets or haikus.

Users who engage in fast-paced movement sessions or who choose "relaxation" focused activities in the midday may often write about stress or work pressures in the evening, possibly reflecting a way they cope with daily stressors.

The system 100 can refine or enhance the recommendations by prompting users 110 for their optimal next activity, which may include not just an activity choice but also duration to perform the activity, time of day to do it. The system 100 can also modify details within the activity, such as choice of colors, rhythms, movement pace, writing length, or the like. Unlike existing recommendation systems, the system 100 can modify the parameters of recommended activities themselves, which can allow for deeper customization based on psychological and emotional inputs rather than just user history or preference.

The system 100 can produce recommendations for the development team in creating new activities. For example, if a majority of users consistently opt for certain musical instruments during their sessions, the system 100 directs developers to create activities that place a spotlight on these instruments. Collaborative filtering can further refine these insights. For instance, if a large cohort of users is integrating nature themes into their writing, and that cohort also shows a preference for slow rhythmic drumming, the system 100 suggests development of an activity that seamlessly integrates forest sounds with drumming.

Success with user engagement relies in a large part on recommending optimal content for that particular user. By being recommended the right content for a user to view next, the user is much more likely to find useful content based on the user's needs, stick with a platform, and use it more often. Advantageously, rich interactive data of the type collected by the system 100 can provide profound, significant user insights that can advance the field of creative therapies research. The system 100 can process and integrate rich data and multimodal data (such as, visual, textual, auditory, or kinesthetic) to tailor recommendations more precisely. This capability extends beyond existing recommendation systems by incorporating emotional and psychological feedback into real-time activity adjustments, thereby enhancing therapeutic efficacy and user engagement.

Figure 5:
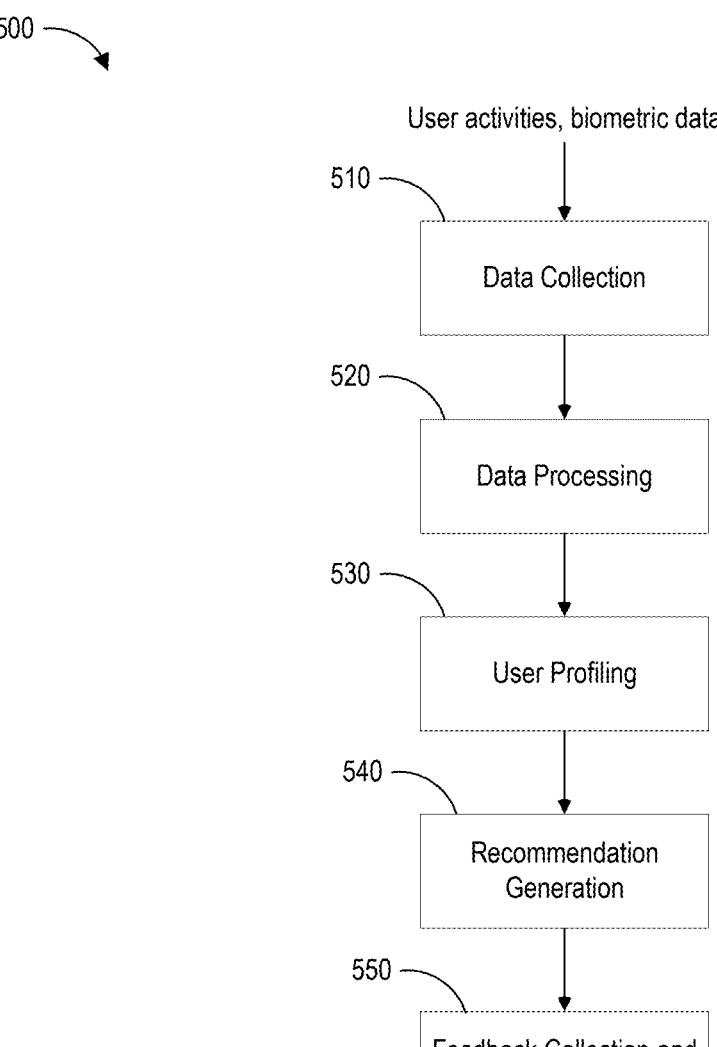
FIG. 5 illustrates a flow chart of a process for providing recommendations by the system illustrated in FIG. 1.

FIG. 5 illustrates a flow chart of a process 500 for providing recommendations. The process 500 can be implemented by the system 100.

The process 500 can begin in block 510 where user data can be collected. As described herein, data from various user interactions, including user inputs during creative activities such as writing, drawing, music-making, or movement, can be collected. Types of collected data can include one or more demographic information, responses to mental health questionnaires, activity selections, time of engagement, modality used (art, music, etc.), emotional feedback (such as, mood ratings post-activity), motion data, and biometric data from one or more sensors (if available).

The process 500 can transition to block 520 where user data can be analyzed and processed. This can include cleaning and preprocessing the data to ensure accuracy and consistency. Cleaning and preprocessing can involve one or more of normalizing data scales, handling missing values, or categorizing unstructured data. Once data has been cleaned and preprocessed, one or more features can be extracted from the data. The one or more features can reflect user preferences and emotional states. For instance, NLP techniques can be used for extracting feature(s) from textual data, image analysis can be used for extracting feature(s) from art, and audio analysis can be used for extracting feature(s) from music. Motion data can include features such as movement speed, patterns, and frequency, which reflect the user's physical engagement and may correlate with emotional states or preferences. Similarly, audio features from music, such as tempo, key, and rhythm, can be analyzed to detect user mood or inclinations, while visual elements in drawings-like color choices, shapes, and brush strokes-offer insight into the user's psychological state.

The process 500 can transition to block 530 and perform user profiling, which can involve developing comprehensive user profiles that encapsulate preferences, behavioral patterns, and psychological needs based on the one or more extracted features and historical data. User profiles can be continuously updated with new data from recent interactions to keep the profiles dynamic and reflective of current user states.

The process 500 can transition to block 540 and generate recommendations for one or more activities. Block 540 can utilize the one or more features extracted in block 520. Block 540 can utilize user profile data from block 530. As described herein, initially, the process 500 can use expert-defined rules to handle the cold start problem and provide generalized recommendations based on psychological principles of creative arts therapies. Once threshold amount of data has been collected, the process 500 can transition to using collaborative filtering, which can identify and apply patterns from similar users to make personalized activity suggestions. Based on the current user profile and specific session feedback (described in connection with block 550), the process 500 can adjust the parameters of the recommended activities. For instance, the process can change the tempo for a music activity based on the user's current energy level.

The process 500 can transition to block 550 and perform feedback collection and adaptation. After one or more recommended activities have been completed by a user, the process 500 can collect user feedback on satisfaction and emotional impact. The process 500 can use such feedback to refine the recommendation generation, thereby enhancing the accuracy and personalization of future recommendations.

Other Variations

Various other configurations are may also be used, with particular elements that are depicted as being implemented in hardware may instead be implemented in software, firmware, or a combination thereof. One of ordinary skill in the art will recognize various alternatives to the specific embodiments described herein.

The specification and figures describe particular embodiments which are provided for ease of description and illustration and are not intended to be restrictive. Embodiments may be implemented to be used in various environments without departing from the spirit and scope of the disclosure.

At least some elements of implementations of one or more disclosed devices of the can be controlled and at least some steps of implementations of one or more disclosed methods can be effectuated, in operation with a programmable processor governed by instructions stored in a memory. The memory may be random access memory (RAM), read-only memory (ROM), flash memory or any other memory, or combination thereof, suitable for storing control software or other instructions and data. Those skilled in the art should also readily appreciate that instructions or programs defining the functions of the disclosed implementations may be delivered to a processor in many forms, including, but not limited to, information permanently stored on non-writable storage media (for example read-only memory devices within a computer, such as ROM, or devices readable by a computer I/O attachment, such as CD-ROM or DVD disks), information alterably stored on writable storage media (for example floppy disks, removable flash memory and hard drives) or information conveyed to a computer through communication media, including wired or wireless computer networks. In addition, while some implementations may be embodied in software, the functions necessary to implement the disclosed features may optionally or alternatively be embodied in part or in whole using firmware and/or hardware components, such as combinatorial logic, Application Specific Integrated Circuits (ASICs), Field-Programmable Gate Arrays (FPGAs) or other hardware or some combination of hardware, software and/or firmware components.

In various embodiments, input from a user may be requested. Examples of methods for receiving user input, such as receiving a button press from a user, are illustrative and not by means of limitation. Alternative methods of receiving user input may be used, including receiving a button press on a touch screen, a physical button press on a device, a swipe, a tap, any other touch gestures, a spoken (audio) input, etc.

Various modifications to the implementations described in this disclosure may be readily apparent to those skilled in the art, and the generic principles defined herein may be applied to other implementations without departing from the spirit or scope of this disclosure. Thus, the claims are not intended to be limited to the implementations shown herein, but are to be accorded the widest scope consistent with this disclosure, the principles and the novel features disclosed herein.

Certain features that are described in this specification in the context of separate implementations also can be implemented in combination in a single implementation. Conversely, various features that are described in the context of a single implementation also can be implemented in multiple implementations separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Depending on the embodiment, certain acts, events, or functions of any of the processes or algorithms described herein can be performed in a different sequence, can be added, merged, or left out altogether. Moreover, in certain embodiments, operations or events can be performed concurrently, for example, through multi-threaded processing, interrupt processing, or multiple processors or processor cores or on other parallel architectures, rather than sequentially.

The various illustrative logical blocks, modules, routines, and algorithm steps described in connection with the embodiments disclosed herein can be implemented as electronic hardware, or as a combination of electronic hardware and executable software. To clearly illustrate this interchangeability, various illustrative components, blocks, modules, and steps have been described above generally in terms of their functionality. Whether such functionality is implemented as hardware, or as software that runs on hardware, depends upon the particular application and design constraints imposed on the overall system. The described functionality can be implemented in varying ways for each particular application, but such implementation decisions should not be interpreted as causing a departure from the scope of the disclosure.

Moreover, the various illustrative logical blocks and modules described in connection with the embodiments disclosed herein can be implemented or performed by a machine, such as a machine learning service server, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A machine learning service server can be or include a microprocessor, but in the alternative, the machine learning service server can be or include a controller, microcontroller, or state machine, combinations of the same, or the like configured to generate and publish machine learning services backed by a machine learning model. A machine learning service server can include electrical circuitry configured to process computer-executable instructions. Although described herein primarily with respect to digital technology, a machine learning service server may also include primarily analog components. For example, some or all of the modeling, simulation, or service algorithms described herein may be implemented in analog circuitry or mixed analog and digital circuitry. A computing environment can include any type of computer system, including, but not limited to, a computer system based on a microprocessor, a mainframe computer, a digital signal processor, a portable computing device, a device controller, or a computational engine within an appliance, to name a few.

The elements of a method, process, routine, or algorithm described in connection with the embodiments disclosed herein can be embodied directly in hardware, in a software module executed by a machine learning service server, or in a combination of the two. A software module can reside in RAM memory, flash memory, ROM memory, EPROM memory, EEPROM memory, registers, hard disk, a removable disk, a CD-ROM, or any other form of a non-transitory computer-readable storage medium. An illustrative storage medium can be coupled to the machine learning service server such that the machine learning service server can read information from, and write information to, the storage medium. In the alternative, the storage medium can be integral to the machine learning service server. The machine learning service server and the storage medium can reside in an ASIC. The ASIC can reside in a user terminal. In the alternative, the machine learning service server and the storage medium can reside as discrete components in a user terminal (for example, access device or network service client device).

Conditional language used herein, such as, among others, "can," "could," "might," "may," "for example," and the like, unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without other input or prompting, whether these features, elements and/or steps are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list.

Disjunctive language such as the phrase "at least one of X, Y, or Z," unless specifically stated otherwise, is otherwise understood with the context as used in general to present that an item, term, etc., may be either X, Y, or Z, or any combination thereof (for example, X, Y, and/or Z). Thus, such disjunctive language is not generally intended to, and should not, imply that certain embodiments require at least one of X, at least one of Y, or at least one of Z to each be present.

Unless otherwise explicitly stated, articles such as "a" or "an" should generally be interpreted to include one or more described items. Accordingly, phrases such as "a device configured to" are intended to include one or more recited devices. Such one or more recited devices can also be collectively configured to carry out the stated recitations. For example, "a processor configured to carry out recitations A, B and C" can include a first processor configured to carry out recitation A working in conjunction with a second processor configured to carry out recitations B and C.

While the above detailed description has shown, described, and pointed out novel features as applied to various embodiments, it can be understood that various omissions, substitutions, and changes in the form and details of the devices or algorithms illustrated can be made without departing from the spirit of the disclosure. As can be recognized, certain embodiments described herein can be embodied within a form that does not provide all of the features and benefits set forth herein, as some features can be used or practiced separately from others. The scope of certain embodiments disclosed herein is indicated by the appended claims rather than by the foregoing description. All changes which come within the meaning and range of equivalency of the claims are to be embraced within their scope.

What is claimed is:

1. A non-transitory computer readable medium storing instructions that, when executed by one or more processors, cause the one or more processors to:

provide a user interface with at least one first input configured to receive first data indicating a set of challenges being faced by a user and at least one second input configured to receive second data indicating a set of strengths of the user;

receive, via the user interface, the first data and the second data;

generate a first query to an application program interface (API) of a large language model (LLM), the first query requesting that the LLM generate a textual narrative about the user in which the set of challenges indicated by the first data is overcome based on the set of strengths indicated by the second data;

provide the first query to the API of the LLM and cause the LLM to generate the textual narrative;

receive the textual narrative from the API in response to providing the first query;

output the textual narrative to the user interface, provide another user interface with at least one third input configured to receive a first poetry line from the user indicative of a problem that the user faces;

receive, via the another user interface, the first poetry line from the user;

generate a second query to the API of the LLM, the second query requesting that the LLM generate a second poetry line responsive to the first poetry line;

provide the second query to the API of the LLM and cause the LLM to generate the second poetry line;

receive the second poetry line from the API in response to providing the second query; and output the second poetry line to the another user interface by appending the second poetry line to the first poetry line.

2. The non-transitory computer readable medium of claim 1, wherein the one or more processors are further caused to:

receive, via the user interface, third data indicating identity of the user; and generate the first query further based on the third data to cause the LLM to generate the textual narrative that further includes the third data.

3. The non-transitory computer readable medium of claim 2, wherein the first query comprises:

a first prompt requesting the LLM to generate the textual narrative about the user identified by the third data;

a second prompt indicating that challenges faced by the user comprise the first data; and a third prompt indicating that strengths of the user comprise the second data.

4. The non-transitory computer readable medium of claim 3, wherein the first query further comprises a fourth prompt specifying a time frame limitation for the textual narrative and a length limitation of the textual narrative.

5. The non-transitory computer readable medium of claim 1, wherein the at least one first input comprises at least one first text box, and wherein the at least one second input comprises at least one second text box.

6. The non-transitory computer readable medium of claim 1, wherein the one or more processors are further caused to:

receive, via the user interface, a third poetry line from the user, the third poetry line being created by the user to maintain a theme and narrative progression of a poem that includes the first and second poetry lines;

generate a third query to the API of the LLM, the third query requesting that the LLM generate a third poetry line responsive to the first, second, and third poetry lines;

provide the third query to the API of the LLM and cause the LLM to generate a fourth poetry line that maintains the theme of the poem;

receive the fourth poetry line from the API in response to providing the third query; and output the fourth poetry line to the another user interface by appending the fourth poetry line to the first, second, and third poetry lines.

7. The non-transitory computer readable medium of claim 1, wherein the one or more processors are further caused to output to the user interface information indicating an intention of generating and outputting the textual narrative prior to receiving the first data and the second data.

8. A non-transitory computer readable medium storing instructions that, when executed by one or more processors, cause the one or more processors to:

provide a user interface for an exercise directed to a therapeutic activity for improving mental wellness of a user;

output to the user interface information indicating an intention of the exercise, the intention indicating a therapeutic concept of the exercise directed to improving mental wellness of the user;

subsequent to outputting information indicating the intention of the exercise, output to the user interface the exercise, the exercise involving user interacting with the user interface;

subsequent to completion of the exercise by the user, prompt the user via the user interface to provide reflective input describing psychological or emotional significance of the exercise experience to the user;

provide on the user interface an input configured to permit the user to draw a challenge; and in response to the user providing a drawing of the challenge via the input, modify the drawing so that the challenge fades away.

9. The non-transitory computer readable medium of claim 8, wherein the therapeutic activity comprises one or more of drawing, writing, dance, or music.

10. The non-transitory computer readable medium of claim 8, wherein the challenge fades away while the user is drawing the challenge.

11. The non-transitory computer readable medium of claim 8, wherein the user interface includes one or more controls configured to adjust one or more parameters of the challenge fading away.

12. The non-transitory computer readable medium of claim 11, wherein the one or more parameters comprise a speed of the challenge fading away.

13. The non-transitory computer readable medium of claim 11, wherein the one or more controls include a slider.

14. A non-transitory computer readable medium storing instructions that, when executed by one or more processors, cause the one or more processors to:

collecting user data related to one or more therapeutic activities for improving mental wellness of a user, the user data comprising one or more of textual data for natural language processing, visual data from user-drawn features, audio data from user-created music, or motion data from user movements;

extract a plurality of features from the user data, the plurality of features reflecting one or more of preferences or emotional states of the user, wherein extracting the plurality of features comprises one or more of: applying natural language processing to textual data, applying visual analysis to user-drawn features, applying audio analysis to user-created music, or applying motion analysis to captured motion data;

based on the plurality of features, generate a recommendation for a therapeutic activity for improving mental wellness of a user by:

in response to a determination that an aggregate data collection threshold across a plurality of users has not been satisfied, apply one or more predefined rules to the plurality of features to generate the recommendation for the therapeutic activity; and in response to a determination that the aggregate data collection threshold across the plurality of users has been satisfied, apply similarity-based analysis to the plurality of features to generate the recommendation for the therapeutic activity; and output the therapeutic activity to a user interface and cause the user to perform the therapeutic activity.

15. The non-transitory computer readable medium of claim 14, wherein the one or more processors are further caused to:

subsequent to completion of the therapeutic activity,
    receive, via the user interface, feedback data relating to
    the therapeutic activity from the user; and
based on the feedback data, adjust a recommendation for
    a subsequent therapeutic activity to be performed by
    the user.

16. The non-transitory computer readable medium of
claim 15, wherein the feedback data includes an adjustment
of a parameter of the therapeutic activity, and wherein the
subsequent therapeutic activity comprises the parameter
modified by the adjustment.

17. The non-transitory computer readable medium of
claim 14, wherein similarity-based analysis comprises:
    grouping the user with at least one another user that shares
        at least one characteristic with the user; and
    generating the recommendation for the therapeutic activ-
        ity based on another therapeutic activity previously
        recommended to the at least one another user.

18. The non-transitory computer readable medium of
claim 14, wherein the therapeutic activity comprises one or
more of drawing, writing, dance, or music.

\*    \*    \*    \*    \*